United States Patent
Palepu et al.

(10) Patent No.: US 8,431,539 B2
(45) Date of Patent: Apr. 30, 2013

(54) FORMULATIONS OF DAPTOMYCIN

(75) Inventors: Nagesh R. Palepu, Southampton, PA (US); Bulusu Bhanu Teja, Hyderabad (IN)

(73) Assignee: Eagle Pharmaceuticals, Inc., Woodcliff Lake, NJ (US)

( * ) Notice: Subject to any disclaimer, the term of this patent is extended or adjusted under 35 U.S.C. 154(b) by 306 days.

(21) Appl. No.: 12/884,653

(22) Filed: Sep. 17, 2010

(65) Prior Publication Data
US 2011/0172167 A1 Jul. 14, 2011

Related U.S. Application Data

(60) Provisional application No. 61/243,402, filed on Sep. 17, 2009, provisional application No. 61/263,695, filed on Nov. 23, 2009.

(51) Int. Cl.
*A61K 38/12* (2006.01)
(52) U.S. Cl.
USPC .......................................................... 514/21.1
(58) Field of Classification Search .................. None
See application file for complete search history.

(56) References Cited

U.S. PATENT DOCUMENTS

| 6,696,412 B1 | 2/2004 | Kelleher et al. |
| 2002/0111311 A1 | 8/2002 | Govardhan et al. |
| 2005/0180925 A1 | 8/2005 | Chaudry |

FOREIGN PATENT DOCUMENTS

EP 0 386 951 * 2/1990

OTHER PUBLICATIONS

SIGMA Buffer Chart, Mar. 2005, accessed online Jan. 11, 2013 at http://medicine.ucsf.edu/labs/brown/protocols_03_2005/sigma_buffer_chart.pdf, 2 pages.*
International Search Report and Written Opinion issued in PCT/US2010/049257 and dated Oct. 22, 2010.

* cited by examiner

*Primary Examiner* — Marcela M Cordero Garcia
(74) *Attorney, Agent, or Firm* — Lucas & Mercanti, LLP

(57) ABSTRACT

Long term storage stable daptomycin-containing compositions are disclosed. The compositions include daptomycin or a pharmaceutically acceptable salt thereof at a concentration of less than or equal to about 25 mg/mL, a buffer having an acidic functional group and have a pH of from about 6.0 to about 7. The formulations are surprisingly free of degradation products such as the hydrolysis product of daptomycin and the β-isomer of daptomycin after storage periods of at least about 18 months.

23 Claims, No Drawings

FORMULATIONS OF DAPTOMYCIN

CROSS-REFERENCE TO RELATED APPLICATIONS

This application claims priority under 35 U.S.C. §119(e) to U.S. Provisional Patent Application No. 61/243,402, filed Sep. 17, 2009, entitled "FORMULATIONS OF DAPTOMYCIN", and to U.S. Provisional Patent Application No. 61/263,695, filed Nov. 23, 2009, entitled "FORMULATIONS OF DAPTOMYCIN", the disclosures of each of which are incorporated by reference herein in their entirety.

BACKGROUND OF THE INVENTION

Daptomycin is a lipopeptide antibiotic represented by the following structural formula (I)

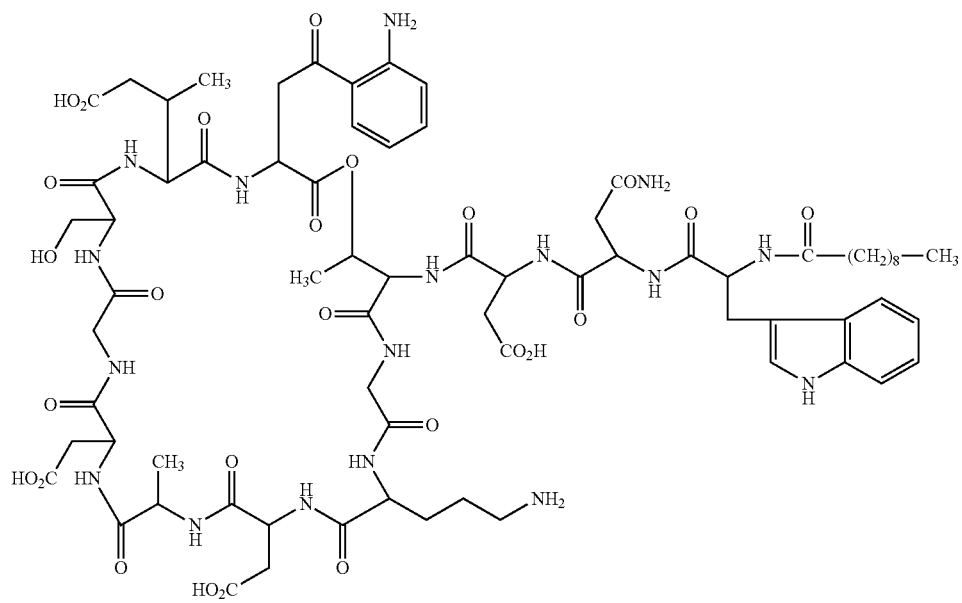

(I)

and is described, for example, in U.S. Pat. No. 4,537,717, the contents of which are incorporated herein by reference.

Daptomycin is used in the treatment of Methicillin-resistant *Staphylococcus aureus* (MRSA) and Methicillin-susceptible *Staphylococcus aureus* (MSSA), *Streptococcus pyogenes, Streptococcus agalactiae, Streptococcus dysgalactiae* subspecies *equisimilis*, and *Enterococcus faecalis* (vancomycin-susceptible isolates only) in complicated skin infections and bloodstream infections (bacteremia), including right-sided infective endocarditis. Daptomycin is commercially available as Cubicin™ for intravenous administration.

Daptomycin exhibits premature degradation upon reconstitution of the lyophilized product. The reconstituted daptomycin exhibits increased degradation after reconstitution and is, therefore, not suitable for long-term storage in liquid form. Some of the main degradants of daptomycin are the hydrolysis product of daptomycin, the β-isomer of daptomycin and anhydro daptomycin. The hydrolysis product (ring opening compound) appears as the main impurity at a Relative Retention Time (RRT) of about 0.66, the β-isomer of daptomycin appears as the main impurity at an RRT of about 0.97 and anhydro daptomycin appears as the main impurity at an RRT of about 1.1. There is a need for daptomycin formulations with increased stability.

SUMMARY OF THE INVENTION

The invention is generally directed to daptomycin-containing compositions that are long term storage stable, i.e. for at least 18 months or longer. In several aspects of the invention, the compositions include a buffer containing an acidic functional group and the concentration of daptomycin in the compositions will be less than or equal to about 25 mg/ml. In other aspects of the invention, the compositions will have a pH of from about 6.0 to about 7. In other aspects of the invention, the compositions include a tonicifying agent. In other aspects of the invention, the compositions include calcium hydroxide.

Still further aspects of the invention include, for example, methods of preparing the compositions and methods of treatment using the compositions.

One of the advantages of the inventive liquid compositions is that they are substantially free of impurities after at least 18 months. Substantially free of impurities refers to daptomycin-containing compositions in which total impurities are less than about 10%, including less than about 5% of the hydrolysis product of daptomycin and less than about 5% of the β-isomer of daptomycin, area-under-the-curve ("AUC") as determined by high performance liquid chromatography ("HPLC") at a wavelength of 223 nm, after a period of at least about 18 months at a temperature of from about 5° C. to about 25° C. The formulations are ready for use or further dilution; storage as a lyophilized powder is no longer a necessity for commercial use of the drug.

DETAILED DESCRIPTION OF THE INVENTION

Unless defined otherwise, all technical and scientific terms used herein have the same meaning as is commonly understood by one of ordinary skill in the art to which this invention belongs. In the event that there are a plurality of definitions for a term herein, those in this section prevail unless stated otherwise.

As used herein, RRT is calculated by dividing the retention time of the peak of interest by the retention time of the main peak. Any peak with an RRT <1 elutes before the main peak, and any peak with an RRT >1 elutes after the main peak.

As used herein, substantially free of impurities refers to daptomycin-containing compositions in which total impurities are less than about 10%, calculated as being based upon the original amount daptomycin (or salt thereof) being present in the composition or formulation. Preferably, the total amount of impurities, i.e. >10% includes less than about 5%, i.e. no more than about ½ thereof, is the hydrolysis product of daptomycin and less than about 5%, i.e. no more than about ½ thereof, is the β-isomer of daptomycin. The amounts of impurities are calculated as area-under-the-curve ("AUC") as determined by high performance liquid chromatography ("HPLC") at a wavelength of 223 nm, after storage periods of at least about 18 months at a temperature of from about 5° C. to about 25° C. In preferred aspects the amount of time the compositions demonstrate long term storage stability is at least about 2 years.

In accordance with one aspect of the invention, there are provided long term storage stable daptomycin-containing compositions, including:
 a) daptomycin or a pharmaceutically acceptable salt thereof at a concentration of less than or equal to about 25 mg/mL; and
 b) a buffer having an acidic functional group.

The compositions have a pH of from about 6.0 to about 7.0; and total impurities are less than about 10%, area-under-the-curve ("AUC") as determined by high performance liquid chromatography ("HPLC") at a wavelength of 223 nm after storage periods of at least about 18 months at a temperature of from about 5° C. to about 25° C. In most of the embodiments described herein, it will be understood that when the daptomycin-containing compositions described herein are referred to as having total impurities of less than about 10%, the compositions will further include less than about 5% of the hydrolysis product of daptomycin and less than about 5% of the β-isomer of daptomycin (as calculated with reference to the original starting amount of daptomycin) after the same period of long term storage, i.e. about 18 months or longer under the conditions mentioned herein.

In some aspects of the invention, the buffer concentration in the compositions is from about 0.02M to about 0.075M. Preferably, the buffer concentration is about 0.05M.

In some aspects of the invention, the acidic functional group in the buffer is a carboxylic or sulfonic group. Thus, as will be appreciated by those of ordinary skill, one can select from among a number of suitable buffers and it is Applicants intention that the scope of the invention includes all such buffers that are capable of being included in daptomycin-containing formulations for extended periods without having a deleterious effect on the drug. Some preferred buffers include ADA (N-(2-acetamido)-2-iminodiacetic acid), ACES (N-(2-acetamindo)-2-amino-ethanesulfonaic acid), PIPES (piperazine-N,N'-bis(2-ethanesulfonic acid)) or MOPSO (3-(N-morpholino)-2-hydroxypropanesulfonic acid). More preferably, the buffer is ADA or PIPES. Preferably, the buffer has a buffer capacity in the pH region of about 6.5 to about 7.0.

In other aspects of the invention, the long term storage stable daptomycin-containing compositions include a tonicifying agent, in amounts which preferably render the composition isotonic or substantially isotonic. Some preferred tonicifying agents include, for example, NaCl, $MgCl_2$ or $CaCl_2$. In some aspects of the invention, the tonicifying agent content in the compositions is less than about 20 mg/ml, i.e. from about 1.5% (v/v) to about 5.0% (v/v). Preferably, the tonicifying agent content is from about 1.5% (v/v) to about 3.0% (v/v), and more preferably, about 1.8% (v/v).

In some aspects of the invention, the inventive compositions are maintained during storage and/or prior to use at a temperature of from about 5° C. to about 15° C. In another embodiment, the compositions are maintained at a temperature of from about 5° C. to about 10° C. More preferably, the compositions are maintained at a temperature of about 5° C., i.e. at about refrigerated temperatures and conditions.

The compositions of the present invention can be kept at a pH of from about 6.25 to about 7.0. Preferably, the pH is about 6.25 to about 6.5. In another embodiment, the compositions are maintained at a pH of about 6.5 to about 6.75. In one embodiment, the pH is about 6.5. In another embodiment, the pH is about 6.75.

In other aspects of the invention, the long term storage stable daptomycin-containing compositions include a pH adjusting agent which is present in an amount sufficient to adjust the pH of the compositions to the ranges set forth above, i.e. from about 6.25 to about 6.75, or to specific points in between such as about 6.5 or about 6.75. One preferred pH adjusting agent is calcium hydroxide. Alternative pH adjusters are those commonly used in the art, including NaOH and HCl.

Without meaning to be bound by any theory or hypothesis, it is been surprisingly found that daptomycin is predominantly ionized at pHs of from about 6.5 to about 7.0. As a result the molecule is considerably more stable and thus self association and degradation thereof is unexpectedly and substantially reduced for extended periods of time.

The amount of daptomycin included in the compositions of the present invention are generally in concentrations of from about 1 mg/mL to about 25 mg/mL. In another embodiment, of the invention, the daptomycin concentration is from about 10 mg/mL to about 25 mg/mL. Alternatively, it can be from about 5 mg/mL to about 20 mg/mL. In yet another embodiment, the daptomycin concentration is from about 7.5 mg/mL to about 15 mg/mL. Preferably, the daptomycin concentration is about 10 mg/mL.

Some preferred embodiments of the invention include daptomycin-containing compositions in which the total amount of impurities are less than about 8% and more preferably less than about 6% area-under-the-curve ("AUC") as determined by high performance liquid chromatography ("HPLC") at a wavelength of 223 nm after a storage period of about 18 months at a temperature of from about 5° C. to about 25° C.

The compositions of the present invention can be self preserved to maintain stability and sterility. Alternatively, the compositions can include one or more art recognized preservatives in amounts generally recognized as being effective for such purposes.

A further embodiment of the invention includes long term storage stable daptomycin-containing compositions which include:
 a) daptomycin or a pharmaceutically acceptable salt thereof at a concentration of about 10 mg/mL; and
 b) ADA, i.e. (N-(2-acetamido)-2-iminodiacetic acid).

These compositions have a pH of from about 6.25 to about 6.5; and have the same stability profiles as already described, i.e. having less than about 10% total impurities, and preferably including less than about 5% of the hydrolysis product of daptomycin and less than about 5% of the β-isomer of daptomycin, area-under-the-curve ("AUC") as determined by high performance liquid chromatography ("HPLC") at a wavelength of 223 nm, after storage at least about 18 months at a temperature of from about 5° C. to about 25° C.

Other compositions in accordance with the present invention include:
a) daptomycin or a pharmaceutically acceptable salt thereof at a concentration of about 10 mg/mL; and
b) PIPES, i.e. (piperazine-N,N'-bis(2-ethanesulfonic acid)).

Unlike the pH ranges recited immediately above, the compositions in this embodiment have a pH in the range of from about 6.25 to about 6.75. The stability profile is the same as previously mentioned, i.e. having less than about 10% total impurities, etc.

A further embodiment of the invention includes daptomycin-containing compositions having similar long term stability profiles but include:
a) daptomycin or a pharmaceutically acceptable salt thereof at a concentration of about 10 mg/mL;
b) ADA; and
c) a tonicifying agent such as NaCl, $MgCl_2$ and $CaCl_2$.

The pH of these compositions is from about 6.25 to about 6.5 and the impurity profile is the same that mentioned above.

A similar composition is one in which the buffer is changed to PIPES and the acceptable range for the pH is from about 6.25 to about 6.75.

A further embodiment of the invention includes daptomycin-containing compositions which have a pH of from about 6.5 to about 6.75; daptomycin or a pharmaceutically acceptable salt thereof at a concentration of about 10 mg/mL; PIPES; and calcium hydroxide. These compositions also have the low levels of impurities and long term stability mentioned herein.

Similar to the above in terms of pH and impurity profile are compositions which include daptomycin or a pharmaceutically acceptable salt thereof at a concentration of about 10 mg/mL; ADA; and calcium hydroxide.

Another embodiment of the invention includes methods of treating daptomycin sensitive diseases in mammals. The methods include administering, to a mammal in need thereof, an effective amount of a daptomycin-containing composition described herein. Since the active ingredient portion of the inventive compositions is an FDA-approved drug, those of ordinary skill will recognize that the doses of daptomycin employed in this aspect of the invention will be similar to those employed in any treatment regimens designed for daptomycin as marketed under the trade name Cubicin™. The patient package insert containing dosing information is incorporated herein by reference. The methods of treatment also include administering the inventive formulations for any purpose or physical condition for which daptomycin has been indicated as being useful.

Another embodiment of the invention includes methods of preparing daptomycin-containing compositions described herein. The methods include reconstituting lyophilized daptomycin to a concentration of less than or equal to about 25 mg/mL in a buffer having an acidic group, and adjusting the pH of the composition to about 6.0 to about 7.0. The steps are carried out under pharmaceutically acceptable conditions for sterility and manufacturing. The reconstitution of the daptomycin can also be carried out with the buffer and a sufficient amount of an aqueous solution.

In a further aspect of the invention, there are provided methods of controlling or preventing the formation of impurities in daptomycin-containing compositions during long term storage. The methods include combining an amount of daptomycin or a pharmaceutically acceptable salt thereof with a sufficient amount of a buffer having an acidic group so that a formulation or composition is formed wherein the amount of daptomycin or pharmaceutically acceptable salt thereof included therein is at a concentration of less than or equal to about 25 mg/ml and the pH of the resultant formulation is from about 6.0 to about 7.0. Further optional steps in accordance therewith include transferring one or more pharmaceutically acceptable doses of the formulations into a suitable sealable container and storing the sealed container at a temperature of from about 5° C. to about 25° C. As a result of carrying out these steps, it is possible to control or substantially prevent the formation of impurities which otherwise occur with daptomycin-containing compositions during long term storage so that the artisan is provided with daptomycin-containing formulations having less than about 10% total impurities area-under-the-curve ("AUC") as determined by high performance liquid chromatography ("HPLC") at a wavelength of 223 nm, after at least about 18 months of storage at a temperature of from about 5° C. to about 25° C. More importantly, the method described herein provides compositions or formulations in which the less than about 10% total impurities is comprised of less than about 5% of the hydrolysis product of daptomycin and less than about 5% of the β-isomer of daptomycin, based on the initial amount daptomycin included in the composition.

The compositions of the present invention can be packaged in any suitable sterile vial or container fit for the sterile storage of a pharmaceutical such as daptomycin. Suitable containers can be glass vials, polypropylene or polyethylene vials or other special purpose containers and be of a size sufficient to hold one or more doses of daptomycin.

A further aspect of the invention includes a kit containing the daptomycin-containing compositions described herein. As will be appreciated by those of ordinary skill, the kit will contain at least one pharmaceutically acceptable vial or container containing one or more doses of the daptomycin-containing compositions as well as other pharmaceutically necessary materials for storing and/or administering the drug, including instructions for storage and use, infusion bag or container with normal saline or $D_5W$, additional diluents, if desired, etc.

EXAMPLES

The following examples serve to provide further appreciation of the invention but are not meant in any way to restrict the effective scope of the invention.

Example 1

ACES, MOPSO, BIS-TRIS, ADA and PIPES buffers were prepared by dissolving buffer in water to achieve 0.05M solutions. The pH of each of the buffers was adjusted to 6.75. NaOH was used to adjust the pH for ACES, MOPSO, ADA and PIPES buffer solutions, whereas HCl was used to adjust the pH for BIS-TRIS buffer solution. Unlike ACES, MOPSO, ADA and PIPES buffers, BIS-TRIS does not have an acidic functional group. Daptomycin was added to each of the buffer solutions to obtain a daptomycin concentration to greater than 10 mg/ml, and the pH was readjusted to 6.75. The solutions were then diluted with buffer to obtain a final daptomycin concentration of 10 mg/ml. The samples were stored at the temperatures indicated in Table 1 below.

Samples were tested for impurities after initial preparation, and at times indicated in Table 1 below. The samples were tested via HPLC at a wavelength of 223 nm, and the amount of daptomycin in the initial sample and the relative retention times (RRT) for each of the hydrolysis product of daptomycin (0.66), the β-isomer of daptomycin (0.97) and anhydro-daptomycin (1.1) were added to obtain the total impurities area-under-the-curve ("AUC") after storage. The test data is reported in Table 1 below.

TABLE 1

Stability of Daptomycin Solutions in Different Buffers at pH 6.75

| Formulation | Temp. | Time Period | Conc. (mg/mL) | % of Initial | Total Imp. % |
|---|---|---|---|---|---|
| Daptomycin + ACES buffer | | Initial | 10.6 | 100 | 4.02 |
| | 15° C. | 2 W | 10.4 | 98.1 | 6.18 |
| | | 1 M | 10.2 | 96.2 | 6.25 |
| | 10° C. | 2 W | 10.5 | 99.1 | 5.98 |
| | 5° C. | 1 M | 10.6 | 100 | 3.97 |
| Daptomycin + MOPSO buffer | | Initial | 10.1 | 100 | 4.03 |
| | 15° C. | 2 W | 10.1 | 100 | 5.76 |
| | 5° C. | 1 M | 10.0 | 99.0 | 4.54 |
| Daptomycin + ADA buffer | | Initial | 9.6 | 100 | 4.23 |
| | 5° C. | 1 M | 9.74 | 101.5 | 4.43 |
| Daptomycin + PIPES buffer | | Initial | 10.5 | 100 | 3.88 |
| | 15° C. | 2 W | 10.4 | 99.1 | 5.52 |
| | | 1 M | 10.4 | 99.1 | 6.48 |
| | 10° C. | 2 W | 10.3 | 98.1 | 4.14 |
| | | 1 M | 10.5 | 100 | 5.05 |
| | 5° C. | 1 M | 10.4 | 99.1 | 4.31 |
| Daptomycin + BIS-TRIS buffer | | Initial | 10.3 | 100 | 4.03 |
| | 15° C. | 2 W | 9.9 | 96.1 | 6.25 |
| | 5° C. | 1 M | 10.1 | 98.1 | 4.58 |

As shown in Table 1, the daptomycin formulations are very stable in solutions containing the buffers having an acidic group. Table 1 shows that daptomycin, when reconstituted at a concentration of about 10 mg/mL, a pH of about 6.75 with a buffer having an acidic group, and stored at 5° C., had substantially no increase in total impurities. The degradation for these samples was limited to a degradation rate of about 0.3% to about 0.5% after 1 month storage at 5° C. In contrast, the BIS-TRIS buffer sample did not satisfy this degradation profile. The BIS-TRIS buffer sample exceeded the desired degradation rate, having a 0.55% increase in impurities after 1 month storage at 5° C.

Example 2

Daptomycin was added to 0.05M ADA buffer solution to obtain a daptomycin concentration of 10 mg/ml, and the pH was adjusted as indicated in Table 2 below with 1N NaOH. The samples were stored at the temperatures indicated in Table 2 below.

Samples were tested for impurities after initial preparation, and at times indicated in Table 2 below. The samples were tested via HPLC at a wavelength of 223 nm, and the amount of daptomycin in the initial sample and the relative retention times (RRT) for each of the hydrolysis product of daptomycin (0.66), the β-isomer of daptomycin (0.97) and anhydro-daptomycin (1.1) were added to obtain the total impurities area-under-the-curve ("AUC") after storage. The test data is reported in Table 2 below.

TABLE 2

Stability of Daptomycin Solutions in 0.05M ADA Buffer

| Formulation | Temp. | Time Period | Conc. (mg/mL) | % of Initial | Total Imp. % |
|---|---|---|---|---|---|
| pH 6.0 | | Initial | 9.80 | 100.0 | 4.20 |
| | 10° C. | 15 d | 9.81 | 100.1 | 4.83 |
| | | 1 M | 9.82 | 100.2 | 5.19 |
| | 5° C. | 1 M | 9.80 | 100.0 | 4.16 |
| | | 3 M | 9.80 | 100.0 | 5.52 |
| pH 6.25 | | Initial | 10.0 | 100.0 | 4.15 |
| | 10° C. | 15 d | 10.0 | 100.0 | 4.68 |
| | | 1 M | 9.87 | 98.7 | 4.98 |
| | 5° C. | 1 M | 10.1 | 101.0 | 4.14 |
| | | 3 M | 9.91 | 99.1 | 5.30 |
| pH 6.5 | | Initial | 10.1 | 100.0 | 4.37 |
| | 10° C. | 15 d | 9.85 | 97.5 | 4.75 |
| | | 1 M | 9.72 | 96.2 | 5.78 |
| | 5° C. | 1 M | 10.0 | 99.0 | 4.22 |
| | | 3 M | 9.77 | 96.7 | 5.39 |
| pH 6.75 | | Initial | 9.60 | 100.0 | 4.23 |
| | 10° C. | 15 d | 9.56 | 99.6 | 4.96 |
| | | 1 M | 9.40 | 97.9 | 5.86 |
| | 5° C. | 1 M | 9.74 | 101.5 | 4.43 |
| | | 3 M | 9.59 | 99.9 | 5.77 |
| pH 7.0 | | Initial | 9.80 | 100.0 | 4.31 |
| | 10° C. | 15 d | 9.80 | 100.0 | 4.79 |
| | | 1 M | 9.71 | 99.1 | 5.70 |
| | 5° C. | 1 M | 9.93 | 101.3 | 4.61 |
| | | 3 M | 9.72 | 99.2 | 6.23 |

As shown in Table 2, the ADA buffer system stabilized daptomycin-containing solutions between pH 6.0 and 6.75. The area % of the total impurities increased about 1.32% at a pH of 6.0, about 1.15% at a pH of 6.25 and about 1.02% at a pH of 6.5 at the end of three months analysis at 5° C. Such an increase projects a shelf-life of about 24 months under refrigerated conditions with levels of impurities within the levels required herein.

The area % of the total impurities increased about 1.54% at a pH of 6.75 and about 1.92% at a pH of 7.0 at the end of three months analysis at 5° C., which projects a shelf-life of about 18 months. It can be seen that these formulations are also therefore within the scope of the invention since they are expected to have long term stability and low levels of impurities when stored for the time periods of at least about 18 months at temperatures below 25° C.

Example 3

Daptomycin was added to 0.05M ADA buffer solution to obtain a daptomycin concentration of 10 mg/ml. The pH was adjusted to 6.75 with 1N NaOH. Solutions were made isotonic with tonicity adjusting agents, NaCl and $MgCl_2$, as indicated in Table 3 below. The samples were stored at the temperatures indicated in Table 3 below.

Samples were tested for impurities after initial preparation, and at times indicated in Table 3 below. The samples were tested via HPLC at a wavelength of 223 nm, and the amount of daptomycin in the initial sample and the relative retention times (RRT) for each of the hydrolysis product of daptomycin (0.66), the β-isomer of daptomycin (0.97) and anhydro-daptomycin (1.1) were added to obtain the total impurities area-under-the-curve ("AUC") after storage. The test data is reported in Table 3 below.

TABLE 3

Stability of Daptomycin Solutions in 0.05M ADA Buffer with Tonicifying Agents

| Formulation | Temp. | Time Period | Conc. (mg/mL) | % of Initial | Total Imp. % |
|---|---|---|---|---|---|
| 0.05M ADA + |  | Initial | 9.70 | 100.0 | 4.37 |
| 10 mg/ml | 10° C. | 15 d | 9.60 | 99.0 | 5.36 |
| daptomycin + |  | 1 M | 9.53 | 98.2 | 5.36 |
| NaCl | 5° C. | 1 M | 9.66 | 99.6 | 4.24 |
|  |  | 3 M | 9.43 | 97.2 | 5.86 |
| 0.05M ADA + |  | Initial | 9.60 | 100.0 | 4.60 |
| 10 mg/ml | 10° C. | 15 d | 9.48 | 98.8 | 5.80 |
| daptomycin + |  | 1 M | 9.32 | 97.1 | 5.91 |
| $MgCl_2$ | 5° C. | 1 M | 9.77 | 101.8 | 4.40 |
|  |  | 3 M | 9.84 | 102.5 | 6.23 |

As shown in Table 3, the buffer systems including tonicifying agents stabilized daptomycin-containing solutions at pH 6.75. The area % of the total impurities increased about 1.49% at the end of three months analysis at 5° C. with the addition of NaCl and 1.63% with the addition of $MgCl_2$. Such increases project a shelf-life of greater than about 18 months with levels of impurities below those required herein, i.e. less than 10% total, etc. Thus, the presence of a tonicity adjusting agent did not adversely affect the solution stability of daptomycin.

Example 4

Daptomycin was added to 5 mg/ml PIPES or 2 mg/ml ADA buffer solution to obtain a daptomycin concentration of 10 mg/ml, and the pH was adjusted as indicated in Table 4 below with calcium hydroxide. The samples were stored at the temperatures indicated in Table 4 below.

Samples were tested for impurities after initial preparation, and at times indicated in Table 4 below. The samples were tested via HPLC at a wavelength of 223 nm, and the amount of daptomycin in the initial sample and the relative retention times (RRT) for each of the hydrolysis product of daptomycin (0.66), the β-isomer of daptomycin (0.97) and anhydro-daptomycin (1.1) were added to obtain the total impurities area-under-the-curve ("AUC") after storage. The test data is reported in Table 4 below.

TABLE 4

Stability of Daptomycin Solutions with Calcium Hydroxide

| Formulation | Temp. | Time Period | Conc. (mg/mL) | % of Initial | Total Imp. % |
|---|---|---|---|---|---|
| PIPES + |  | Initial |  | 9.88 | 100.0 | 3.48 |
| pH 6.5 | 10° C. | 1 M | 9.87 | 99.9 | 4.49 |
|  |  | 1.5 M | 9.80 | 99.2 | 4.72 |
|  |  | 2 M | 9.72 | 98.4 | 4.80 |
|  |  | 2.5 M | 9.71 | 98.3 | 4.98 |
|  |  | 3 M | 9.50 | 96.2 | 5.95 |
|  | 5° C. | 1 M | 8.16 | 82.6 | 3.19 |
|  |  | 2 M | 8.15 | 82.5 | 4.14 |
|  |  | 3 M | 7.72 | 78.1 | 4.28 |
| PIPES + |  | Initial | 9.71 | 100.0 | 3.55 |
| pH 6.75 | 10° C. | 1 M | 9.68 | 99.7 | 4.23 |
|  |  | 1.5 M | 9.52 | 98.0 | 4.45 |
|  |  | 2 M | 9.54 | 98.2 | 4.69 |
|  |  | 2.5 M | 7.15 | 73.6 | 5.21 |
|  |  | 3 M | 6.77 | 69.7 | 5.91 |
|  | 5° C. | 1 M | 9.75 | 100.4 | 3.98 |
|  |  | 2 M | 9.68 | 99.7 | 4.10 |
|  |  | 3 M | 9.55 | 98.4 | 4.06 |
| ADA + |  | Initial | 9.78 | 100.0 | 3.73 |
| pH 6.5 | 10° C. | 1 M | 8.29 | 84.8 | 4.90 |
|  |  | 1.5 M | 7.16 | 73.2 | 5.04 |
|  | 5° C. | 1 M | 7.88 | 80.6 | 4.12 |
| ADA + |  | Initial | 9.83 | 100.0 | 3.55 |
| pH 6.75 | 10° C. | 1 M | 6.07 | 61.7 | 4.63 |
|  |  | 1.5 M | 7.98 | 81.2 | 5.21 |
|  | 5° C. | 1 M | 7.62 | 77.5 | 4.04 |

As shown in Table 4, the buffer-containing formulations pH adjusted with calcium hydroxide stabilized daptomycin-containing solutions between pH 6.5 and 6.75. The area % of the total impurities in the PIPES buffer system increased about 0.8% at a pH of 6.5 and about 0.51% at a pH of 6.75 at the end of three months analysis at 5° C. The area % of the total impurities in the ADA buffer system did not increase at the end of one month analysis at 5° C. Such increases project a shelf-life of greater than 24 months under refrigerated conditions with levels of impurities within the ranges required herein.

We claim:

1. A long term storage stable daptomycin-containing composition, comprising:
    daptomycin or a pharmaceutically acceptable salt thereof at a concentration of less than or equal to about 25 mg/mL;
    b) buffer having an acidic functional group,
    c) calcium hydroxide,
    said composition having a pH of from about 6.0 to about 7.0;
    said daptomycin-containing composition having less than about 10% total impurities, area-under-the-curve ("AUC") as determined by high performance liquid chromatography ("HPLC") at a wavelength of 223 nm, after at least about 18 months of storage at a temperature of from about 5° C. to about 25° C.

2. The long term storage stable daptomycin-containing composition of claim 1, wherein the less than about 10% total impurities include less than about 5% of the hydrolysis product of daptomycin and less than about 5% of the β-isomer of daptomycin, based on the amount daptomycin included in said composition.

3. The long term storage stable daptomycin-containing composition of claim 1, wherein the buffer concentration is from about 0.02M to about 0.075M.

4. The long term storage stable daptomycin-containing composition of claim 3, wherein the buffer concentration is about 0.05M.

5. The long term storage stable daptomycin-containing composition of claim 1, wherein the buffer is selected from the group consisting of ADA (N-(2-acetamido)-2-iminodi acetic acid), ACES (N-(carbamoylmethyl)-2-amino-ethane-sulfonaic acid), PIPES (piperazine-N,N'-bis(2-ethane-sulfonic acid)) and MOPSO (3-(N-morpholino)-2-hydrox-propanesulfonic acid).

6. The long term storage stable daptomycin-containing composition of claim 1, further comprising a tonicifying agent.

7. The long term storage stable daptomycin-containing composition of claim 6, wherein the tonicifying agent is selected from the group consisting of NaCl, $MgCl_2$ and $CaCl_2$.

8. The long term storage stable daptomycin-containing composition of claim 6, wherein the amount of tonicifying agent content in the composition is from about 1.5% (v/v) to about 5.0% (v/v).

9. The long term storage stable daptomycin-containing composition of claim 8, wherein the amount of tonicifying agent in the composition is about 1.8% (v/v).

10. The long term storage stable daptomycin-containing composition of claim 1, wherein the composition is maintained at a temperature of from about 5° C. to about 15° C. during storage.

11. The long term storage stable daptomycin-containing composition of claim 10, wherein the composition is maintained at a temperature of from about 5° C. to about 10° C. during storage.

12. The long term storage stable daptomycin-containing composition of claim 11, wherein the composition is maintained at a temperature of about 5° C. during storage.

13. The long term storage stable daptomycin-containing composition of claim 1, wherein the pH is from about 6.25 to about 6.75.

14. The long term storage stable daptomycin-containing composition of claim 13, wherein the pH is about 6.5.

15. The long term storage stable daptomycin-containing composition of claim 1, wherein the daptomycin concentration is from about 1 mg/mL to about 25 mg/mL.

16. The long term storage stable daptomycin-containing composition of claim 15, wherein the daptomycin concentration is from about 7.5 mg/mL to about 15 mg/mL.

17. The long term storage stable daptomycin-containing composition of claim 16, wherein the daptomycin concentration is about 10 mg/mL.

18. The long term storage stable daptomycin-containing composition of claim 1, wherein said long term storage is at least about 2 years.

19. A long term storage stable daptomycin-containing composition, comprising:
   a) daptomycin or a pharmaceutically acceptable salt thereof at a concentration of about 10 mg/mL;
   b) ADA (N-(2-acetamido)-2-iminodiacetic acid); and
   c) calcium hydroxide;

said composition having a pH of about 6.5; and having less than about 10% total impurities, area-under-the-curve ("AUC") as determined by high performance liquid chromatography ("HPLC") at a wavelength of 223 nm, after at least about 18 months storage at a temperature of from about 5° C. to about 25° C.

20. The long term storage stable daptomycin-containing composition of claim 19, wherein the less than about 10% total impurities include less than about 5% of the hydrolysis product of daptomycin and less than about 5% of the β-isomer of daptomycin, based on the amount daptomycin included in said composition.

21. A long term storage stable daptomycin-containing composition, comprising:
   a) daptomycin or a pharmaceutically acceptable salt thereof at a concentration of about 10 mg/mL;
   b) PIPES (piperazine-N,N'-bis(2-ethanesulfonic acid)); and
   c) calcium hydroxide;

said composition having a pH of about 6.75; and having less than about 10% total impurities, area-under-the-curve ("AUC") as determined by high performance liquid chromatography ("HPLC") at a wavelength of 223 nm, after at least about 18 months storage at a temperature of from about 5° C. to about 25° C.

22. The long term storage stable daptomycin-containing composition of claim 21, wherein the less than about 10% total impurities include less than about 5% of the hydrolysis product of daptomycin and less than about 5% of the β-isomer of daptomycin, based on the amount daptomycin included in said composition.

23. A method of treating a daptomycin sensitive disease in mammals, comprising administering an effective amount of a long term storage stable daptomycin-containing composition of claim 1 to a mammal in need thereof.

* * * * *